US006436423B1

(12) United States Patent
Ballinger, Jr. et al.

(10) Patent No.: US 6,436,423 B1
(45) Date of Patent: *Aug. 20, 2002

(54) PRODUCT AND METHOD FOR IMPROVING AVIAN HEALTH

(75) Inventors: Kenneth E. Ballinger, Jr., Kennett Square, PA (US); Craig W. Henry, Brunswick, ME (US)

(73) Assignee: Arkion Life Sciences, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/333,329

(22) Filed: Jun. 15, 1999

Related U.S. Application Data

(60) Provisional application No. 60/092,149, filed on Jul. 9, 1998.

(51) Int. Cl.[7] ............................................... A01N 25/12
(52) U.S. Cl. ..................... 424/409; 424/413; 424/421; 424/406; 514/679; 514/680; 514/681; 514/682; 514/688; 514/918; 514/920
(58) Field of Search ................................ 424/405, 409, 424/406, 407, 410–413, 414, 417–421; 514/918, 920, 679–682, 688

(56) References Cited

U.S. PATENT DOCUMENTS

| | | | | |
|---|---|---|---|---|
| 4,376,422 A | * | 3/1983 | Whitehead et al. | 119/1 |
| 4,790,990 A | * | 12/1988 | Mason et al. | 424/438 |
| 5,195,465 A | | 3/1993 | Webb et al. | 119/172 |
| 5,352,780 A | | 10/1994 | Webb et al. | 536/56 |
| 5,385,842 A | | 1/1995 | Weimer et al. | 435/262 |
| 5,500,368 A | | 3/1996 | Tatnall | 435/262 |
| 5,648,258 A | | 7/1997 | Odom | 435/252.1 |
| 5,728,898 A | | 3/1998 | Krackov | 568/763 |
| 5,792,468 A | * | 8/1998 | Belant et al. | 424/409 |
| 5,865,143 A | | 2/1999 | Moore, Jr. | 119/442 |
| 5,885,604 A | | 3/1999 | Ballinger, Jr. | 424/405 |
| 5,922,774 A | | 7/1999 | Winslow | 514/680 |
| 5,956,880 A | * | 9/1999 | Sugimoto | 43/2 |

FOREIGN PATENT DOCUMENTS

EP 0666027 * 9/1995

* cited by examiner

*Primary Examiner*—Neil S. Levy
(74) *Attorney, Agent, or Firm*—Basil S. Krikelis

(57) ABSTRACT

A product and method for reducing and preventing the ingestion of substrates by avians wherein the substrates are disposed within an avian house. The product is a bird repellent in combination with a substrate disposed within an avian house. As a result of the reduced ingestion of substrates such as litter, healthier avians are achieved.

2 Claims, No Drawings

PRODUCT AND METHOD FOR IMPROVING AVIAN HEALTH

RELATED APPLICATIONS

This application claims the benefit of U.S. Provisional Application No. 60/092,149, filed on Jul 9, 1998.

FIELD OF THE INVENTION

The invention generally relates to the improvement of avian health. More particularly, the invention relates to a product comprising the combination of a bird repellent and a substrate, and more specifically litter, which, when applied within an avian house keeps avians from pecking the substrate, resulting in the production of healthier birds.

BACKGROUND OF THE INVENTION

Poultry raised commercially by intensive farming methods uses high-density growth conditions that can mitigate disease through the vector of the poultry house and, more particularly, the litter. The poultry house floor is basically a substrate for the poultry to stand on and provides a natural target for pecking. In addition, birds peck the litter as they would naturally peck the ground in search of food and grit for their gizzard. Grit is used in a bird's gizzard as a means to grind food. As birds ingest products deposited throughout the poultry house, and particularly in the litter, certain pathogenic organisms such as bacteria, viruses and parasites are introduced into the bird's system. As an example, the common disease coccidiosis is transmitted from bird to bird through feces that is mingled with litter and then ingested by the birds. It is also known in the industry that ingestion of litter by commercially raised poultry is a common source of several other diseases caused by pathogens such as Salmonella, Clostridia and other endoparasites, viruses and bacteria.

Presently, treatment for such diseases includes the addition of anticoccidials and any other medications to feed and/or water for the treatment and/or prevention of such specific pathogen based diseases. Other common medications for such diseases include antibiotics such as, for example, ionophores, which include Salinomycin and Monensin.

SUMMARY OF THE INVENTION

The present invention is a product and method for the multifunctional treatment of substrates within avian houses that improves avian performance. More specifically, the invention comprises the use of a bird repellent applied to any of a variety of substrates, and most preferably litter, located within avian houses. Such bird repellent-coated avian house substrates are effective in the following aspects:

One aspect of the invention is the reduction and prevention of litter and other substrate ingestion by avians in an avian house such that the disease exposure in those avians is significantly lowered.

Another aspect of the invention is that due to a reduction in litter and other substrate ingestion, the avians in the avian house have overall improved health.

An additional aspect of the invention is that due to the reduction in litter and other substrate ingestion, there is a resulting improvement in weight adjusted feed efficiency of avians.

The final aspect of the invention is that in the specific case of litter coated with a polycychic quinone compound, there is a resulting inhibition of sulfide generation by the litter, which, as a result, improves the odor conditions and lowers sulfide odors which may occur in a poultry house.

DETAILED DESCRIPTION OF THE INVENTION

Definitions

The term "litter" means any material or covering used to provide a bed (syn. bedding material, bedding) for animals. (some examples of litter include wood shavings, rice hulls, and straw among others).

The term "avian" means any warm-blooded egg laying, feathered vertebrate provided with wings (syn. Bird).

The term "poultry" means any domestic fowl reared for the table, or their eggs or feathers including broilers, fryers, cocks and hens, capons, turkeys, ducks, geese and any others.

The term "avian house" means any building used to house or shelter poultry for any reason (syn. hen house, chicken coop, coop, hen coop, grow out barn, breeder house).

The term "weight adjusted feed efficiency" is based upon a feed efficiency corrected to a standard weight called the "weight adjusted feed efficiency" (WAFE). Feed efficiency can be adjusted to a standard weight of 2.00 kg. For every 31.78 grams difference in weight, the feed efficiency can be adjusted by 0.01. For example:

a) If the actual weight is higher than the standard weight then the feed efficiency is adjusted downward. If the actual weight is lower than the standard weight then the feed efficiency is adjusted upward. For example:

b) Assume a treatment group has an average weight of 2.032kg with a 2.0 feed efficiency.

c) Based upon an efficiency factor of 31.78 grams of weight equaling 0.01kg of feed efficiency then the WAFE would equal 1.99 for a standard with of 200kg.

The term "improved avian health" means any improvement in mortality (livability), and/or morbidity and/or condemnations.

The term "condemnation" means avian whole bodies, body parts or avian products (further processed meat, eggs etceteras) found unacceptable for human consumption by the governing meat and poultry inspection service.

The term "improved avian performance" means any improvement in an economic parameter used to determine improved revenues from the sale or barter of avian products for retail sale. For example, live body weight, carcass weight, salable meat yield, salable eggs, feed efficiency, average daily gain, eggs per hen housed, viable chicks, chicks per hen housed etceteras.

The term "bird repellent" means a compound or preparation that makes a bird select alternate behavior patterns in order to avoid contact, ingestion, odor or the presence of the compound.

The term "polycyclic quinone" or "PCQ" means bicyclic, tricyclic and tetracyclic condensed ring quinones and hydroquinones, as well as precursors thereof.

The term "active form of PCQ" means the formulation or finished state of the PCQ in which the molecule of PCQ is most effective.

The term "raw PCQ" means unprocessed active ingredient.

The term "non-toxic" means a substance judged by he U.S. Environmental Protection Agency as non-toxic by qualified analytical methods.

The term "spreader sticker" means any compound used as an adjuvant for improving the adherence of active ingredients to the surface of a leaf or other plant tissue.

The Invention

The present invention relates to the application of a bird repellant to various substrates within an avian house. It is the inventors' finding that the ability to repel avians from feeding on substrates within an avian house is an effective way to inhibit the uptake of material, such as disease bearing litter. The invention thus has the net result of affecting avian performance in the following manner: (i) improving weight gain and feed efficiency, resulting in an improved weight adjusted feed efficiency; (ii) lowering disease exposure to the avian, (iii) improving avian health; and (iv) in some cases, lowering sulfide odors within an avian house.

As described in greater detail below, the bird repellent can be any compound or substance which has bird repellency properties. The bird repellent can be added to any type of substrate within an avian house for purposes of this invention, a substrate can be any particle or surface found or located within the avian house. For example, it is contemplated that the bird repellent be applied to such substrates as the floor, walls or litter located within an avian house.

Bird Repellent

As mentioned above, any compound or substance which functions as a bird repellent can be used in the invention. The following paragraphs summarize various characteristics of bird repellent compounds which are preferred for use in this invention.

Initially, it is important to the effectiveness of the invention that the bird repellent, in whatever physical form it is applied, be persistent. More particularly, the active material of the applied bird repellent should preferably be able to resist erosion by wind and rain and other environmental forces to which the treated surface may be exposed. For example, it is preferred (1) that the active form of the bird repellent have a relatively low solubility in water so that it is not easily washed off the treated litter surfaces, and (2) that the bird repellent have a relatively high melting temperature so that it does not undergo excessive evaporation from the treated litter surfaces during exposure to high ambient temperatures. For these reasons, it is preferred that the active bird repellent material has a solubility in water under ambient temperature conditions of no more than about 0.001–1000 ppm and preferably in the range of 0.01–200 ppm. The melting temperature of the active bird repellent component should be at least about 150C. and preferably at least 200C.

Even when the active bird repellent material possesses the above-described preferred physical properties, and is maintained in the above-described environmental conditions, the material may still have poor persistence if it does not adhere well to the litter surface to which it is applied. This is a function of the different surface properties of the litter and the bird repellent material.

It is also preferred that the bird repellent be non-toxic to the specific avian with which it will be used. Although not required for the invention non-toxic bird repellent is preferred because although an avian may not peck the bird repellent-coated substrate, it will still stand on it or touch it in various other ways.

Coadjuvants

In an alternative embodiment, a coadjuvant can be used with any bird repellent to give the bird repellent certain properties which allow for more effective application of the bird repellent to the substrate. For instance, coadjuvant, as used herein, may refer to materials which have a bio-activity different than the bird repellents themselves. Such materials include pH adjustment, ammonia control agents, phosphate control agents, trigeminal bird repellents and mixtures thereof Both liquid and solid coadjuvants can be used in conjunction with the bird repellents, depending on the manner of application (See discussion below). Suitable coadjuvants for use with the invention, include Sodium bisulfate, 2-hydroxy acetophenone, limonene and other bird repelling terpenes, methyl anthranalate, alum, zeolytes, calcium sulfate, antibiotics, antiviral agents, inorganic and organic acids, among others.

Sticking Agents:

In an additional alternative embodiment, it is suggested that the bird repellent contain a "sticking agent", i.e., a material which itself has good adhesion to the substrate and when mixed with the bird repellent causes the bird repellent to adhere to the substrate more firmly. Examples of preferred sticking agent include aqueous polymer lattices, which upon evaporation of the water therefrom, form a polymeric mass which is highly adhesive to the litter surface and holds particles of the active material firmly on the litter surface. Such latex sticking agents typically contain a small amount of surfactant dissolved in the aqueous phase. It is noted that any other sticking agent which causes or helps the bird repellent to adhere to the substrate can be used in the invention.

Additives

The inventors contemplate a further alternative embodiment wherein additives are combined with the bird repellent.

As used herein, the term "additives" refers to materials which augment the effectiveness of the bird repellents, but which do not by themselves have bio-activity. These include such materials as surfactants, wetting agents, defoaming agents, extenders, sticking agents, penetrants, plasticizers, activators, spreading agents, diluents, odorants and the like.

Polycyclic Quinone Composition

Although any bird repellent compound can be used in the invention, it is preferred that the bird repellant be a non-ionic polycyclic quinone (PCQ) and, more preferably, a PCQ selected from bi- to tetra-cyclic quinones, hydroquinones and mixtures thereof having (a) a light absorbency within the range of 200–400 nm, (b) solubility in water no higher than 1,000 ppm by weight, (c) a melting point no lower than 102C. and (d) $LD_{50}$ in female rats of at least 2,000 mg/kg.

It is the inventors discovery that the application to the litter repels away an avian by a mechanism of bird repellency as disclosed in U.S. patent application No. US97/05662 by Ballinger et al., which is incorporated herein in its entirety.

A wide variety of polycyclic quinones can be used in the invention. As used herein, the term "polycyclic quinone" or "PCQ" refers to bicyclic, tricyclic and tetracyclic condensed ring quinones and hydroquinones, as well as precursors thereof. On the whole, the non-ionic polycyclic quinones and polycyclic hydroquinones (herein referred to collectively as PCQs) have very low solubility in water at ambient temperatures. For use in the invention, It is preferred that such PCQs have a water solubility no higher than about 1,000 ppm, by weight.

However, as noted above, certain precursors of such PCQs can also be used in the invention either combined with the relatively insoluble PCQs or by themselves. Such precursors include anionic salts of PCQs which are water soluble under alkaline anaerobic conditions. These materials, however, are not stable and are easily converted to the insoluble quinone form upon exposure to air. Thus, when anionic PCQs are applied to litter and exposed to air, they are quickly converted to the water-insoluble, more active quinone form.

Among the water-insoluble PCQs which can be used in the invention are anthraquinones (AQ), such as 1,2- dihydroxy anthraquinone, 1,4-dihydroxy anthraquinone, naphthoquinone, anthrone(9,10-dihydro-9-oxo-anthracene), 10-methylene-anthrone, phenanthrenequinone and the alkyl, alkoxy and amino derivatives of such quinones, 6,11-dioxo-1H-anthra[1,2-c]pyrazole, anthraquinone-1,2-naphthacridone, 7,12-dioxo-7,12-dihydroanthra[1,2-b]pyrazine, 1,2-benzanthraquinone, 2,7-dimethylanthraquinone, 2-methylanthraquinone, 3-methylanthraquinone, 2-aminoanthraquinone and 1-methoxyanthraquinone. Of the foregoing cyclic keytones, anthraquinone and 1,4-dihydroxyanthraquinone are preferred because they appear to be more effective. Naturally occurring AQs can be used as well as synthetic AQs.

Other PCQs which can be used include more soluble AQ compounds such as 1,8-dihydroxy-anthraquinone, 1-amino-anthraquinone, 1-chloro-anthraquinone, 2-chloro-anthraquinone, 2-chloro-3-carboxyl-anthraquinone and 1-hydroxy-anthraquinone. Various ionic derivatives of these materials can be prepared by catalytic reduction in aqueous alkali.

Also within the AQ family are a wide variety of anthrahydroquinone compounds which can be used in the method of the invention. As used herein, the term "anthrahydroquinone compound" refers to compounds comprising the basic tricyclic structure such as 9,10-dihydroanthrahydroquinone, 1,4-dihydroanthrahydroquinone, and 1,4,4a,9a-tetrahydroanthrahydroquinone. Anthrahydroquinone itself is 9,10-dihydroxyanthracene.

Both water-insoluble and water-soluble forms of anthrahydroquinone compounds can be used in the invention. The non-ionic compounds are largely insoluble in aqueous systems, while ionic derivatives, such as di-alkali metal salts, are largely soluble in water. The water soluble forms are stable only in high pH anaerobic fluids. Low pH fluids (pH less than about 9–10) will generally result in the formation of the insoluble molecular anthrahydroquinone. Aerobic solutions will incur oxidation of the anthrahydroquinones to anthraquinone. Thus, anthrahydroquinones will not exist for long periods of time in an aerated environment such as that which is experienced by spraying. For these reasons, anthrahydroquinone treatments are usually implemented with the soluble ionic form in a caustic solution. Sodium hydroxide solutions are preferred over the hydroxides of other alkali metals for economic reasons.

Regarding PCQs in general, the specific PCQ used should be preferably in a physical form small enough to be touched by the sensory organs of the avian and to affect the gut. If the particles are too large, the nerves may pick up the presence of the chemical poorly, if at all. Thus, for the PCQ to be most effective as a repellent, it is preferred that they be of a sufficiently small particle size in order to effectively be sensed by an avian.

In particular, it is preferred that the particles of PCQ be less than about 50 micrometers in diameter and more preferably, that the particles be less than 30 micrometers in diameter . Similarly, smooth continuous surfaces of PCQ cannot be adequately sensed, and, of course, if the PCQ is coated with anything which is non-repellent to the bird or to which the bird is taste insensitive, the PCQ is ineffective. It is preferred that the particles be of sufficient size or have a contour that contains areas that are small enough to be sensed.

When the PCQ is applied directly in particulate form, the size of the particles can be readily controlled. When such particles are applied as a single layer of particles, substantially all of the PCQ would be effective. However, if the particles are applied as a multiple of particle layers, essentially only the top layer would be effective. An important aspect of this analysis is that it is not important that the PCQ be applied as continuous covering.

As mentioned earlier, it is preferred that the bird repellent be non-toxic. PCQ compounds meet this criteria as they are essentially non-toxic, i.e., they have an $LD_{50}$ of at least 2,000 mg/kg in rats and preferably an $LD_{50}$ in rats of 5,000 mg/kg or higher. Because of this low toxicity, PCQs are not toxic to birds, animals and humans. Moreover, the toxicity level is sufficiently low that any active material that becomes leached into the soil will not be detrimental to the normal constituents of fertile soil layers. PCQ's with a degradation half-life of less than 60 days are preferred to insure that no bio-accumulation will occur.

Substrates

As described earlier, it is preferred that the bird repellent of choice be applied to a substrate within an avian house. For purposes of this invention, a substrate means any particle substance upon which a bird repellent can be deposited. Some examples of substrates include flooring, walls and litter disposed within or part of the interior of the house.

Use of such composition comprising a bird repellent and a substrate within an avian house is beneficial in at least four important respects: (1) avians raised thereon have improved health because they consume smaller amounts of the material and/or substrate; (2) the avians exhibit improved feed efficiency and weight gain because of their improved health; (3) the avians have lower mortality and morbidity rates arising out of the lower consumption of material and/or substrate; and (4) as a result of these benefits, higher densities of avians can be raised on whatever area of the substrate is available. Of particular importance is the fact that all of these benefits take place simultaneously merely by raising the avians on such a composition. No special grazing or other environmental conditions are required to obtain these advantages beyond use of the substrate of the invention as the grazing medium.

In a preferred embodiment, the substrate upon which the bird repellent is applied comprises avian litter. It is the inventors' finding that the use of a combination of litter and a bird repellent compound has the net effect of improving the agronomic conditions of avian production raised thereon. Litter comes in many forms, which include bedding materials of either natural or synthetic materials. Examples of such natural materials are grass, hay, straw, grain hulls, wood shavings and saw dust, shredded, macerated or pelletized paper derived from cardboard, Kraft paper or newsprint. Synthetic materials suitable for use as litter include synthetic foamed polymers and inorganic adsorbents such as silica. Upon use as poultry litter, these materials usually become admixed with varying amounts of manure, spilled food and feathers. As discussed hereinbelow, litter is often admixed with various adjuvant materials and additives either prior to or during use.

Other substrates include any flooring or wall materials used in an avian house. The bird repellent can be applied to the floor and/or walls of an avian house to keep the birds from pecking the same.

Methods of Application

The bird repellent compound can be applied to the substrate of interest in any way that allows the invention to work. It is preferred that the substrate of interest be coated and/or saturated with the bird repellent of choice, or precursors thereof, by spraying on the outer surface or, alternatively, by immersing the substrate in a liquid dispersion of the bird repellent or liquid dispersion of a precursor thereof A particularly preferred way of coating the substrate involves direct spraying in which the substrate is coated with the bird repellent or precursor thereof.

The bird repellent of choice can be applied to the substrate of choice in any quantity which is effective. In the particular case of a PCQ bird repellent, it is preferred that fine droplets of the PCQ dispersion formulated to 50% PCQ by weight are sprayed at a rate such that the upper layer of the substrate is treated at a rate between 0.001 gallons per thousand square feet and 10 gallons per thousand square feet and more preferably, between 0.066 gallons per thousand square feet and 0.33 gallons per thousand square feet.

The treating material can also be sprayed onto the substrate while it is fluidized in air. Both bird repellents and precursors thereof can be applied in this manner. Though the substrate can be coated by immersion in the treating solution, this method is not the most preferred because it involves intensive drying. So long as the coating is sufficient to provide an operable amount of the particulate coating, further coating thickness is not needed, for example, in the specific case of PCQ's, only small concentrations of PCQ or PCQ precursor need be applied to the substrate.

The advantageous properties of this invention can be observed by reference to the following examples that illustrate the invention.

EXAMPLES

Example 1

Evaluation Of the Efficacy Of AQ Applied to the Litter Used in Broiler Chicken Houses A total of 3456 one-day-old straight run Ross x Hubbard HyY broiler chicks was used in the experiment. There were 6 treatments with 8 replicates per treatment and 72 birds per replicate. The individual pen was the experimental unit. The experimental treatments used follows:

1. Negative Control =No coccidiostat or growth promoting antibiotics and no litter treatment
2. Positive Control=BioCox® (full dose)+BMD®+3-Nitro and no litter treatment
3. BioCox® (full dose)+BMD®+3-Nitro+0.5x litter treatment*
4. BioCox® (full dose)+BMD®+3-Nitro+1.0x AQ litter treatment**
5. BioCox® (half dose)+BMD®+3-Nitro+0.5x AQ litter treatment
6. BioCox® (half dose)+BMD®+3-Nitro+1.0x AQ litter treatment

*0.5x Solution of AQ–⅛ Gallon/44,000sqft
**1.0x Solution of AQ–¼ Gallon/44,000sqft

TABLE 1

42 Day Data

| Treatment | Weight Gain Kg (42 days) | Feed Efficiency | Mortality % |
|---|---|---|---|
| 1 | 2.134c | 1.796d | 6.338b |
| 2 | 2.232ab | 1.760c | 4.754ab |
| 3 | 2.224ab | 1.761c | 3.345a |
| 4 | 2.249a | 1.725a | 4.577ab |
| 5 | 2.200b | 1.757bc | 4.401ab |
| 6 | 2.231ab | 1.731ab | 2.993a |

*values with the same letters are not significantly different

Results and Conclusions

Results of this trial as set forth in Table 1 above. Table 1 shows that the forty-two day weight gain for the positive control was significantly improved over the negative control ($p<0.05$). Weight gain for treatments 3, 4, 5, and 6, were significantly improved over the negative control ($p<0.05$) but not different from the positive control ($p<0.05$) at 42 days.

Forty-two day feed conversion for the positive control was significantly improved ($p<0.05$) from the negative control. Treatments 3, 4, 5 and 6 indicated significant ($p<0.05$) improvement of feed efficiency over the negative control. Treatments 4 and 6 demonstrated a significant improvement ($p<0.05$) in feed efficiency over the positive control while treatment 5 demonstrated no improvement over the positive control.

Forty-two day mortality for treatments 3, and 6, indicated significant ($p<0.05$) improvement in mortality compared to the negative control. However, treatments 3, 4, 5 and 6, were not different from the positive control.

Based on the data obtained, AQ applied to the litter at the 1.0x dose resulted in an improvement in feed efficiency at both the full dose and half dose of coccidiostat in the feed.

Example 2

Evaluation Of the Efficacy of AQ Applied to the Litter Used in Broiler Chicken Houses A total of 6912 one-day-old straight run Ross x Hubbard HyY broiler chicks was used in the experiment. There were 12 treatments with 8 replicates per treatment and 72 birds per replicate. The individual pen was the experimental unit. The experimental treatments used were as follows:

1. Negative Control—No coccidiostat or growth promoting antibiotics—No litter treatment
4. No litter treatment—BioCox (half dose)
3. 4x AQ litter treatment—No feed additives
4. 4x AQ litter treatment—BioCox (half dose)
5. 10.0x AQ litter treatment—No feed additives
6. 4.0x AQ litter treatment+BioCox (low dose)+BMD+3-Nitro
7. 4.0x AQ litter treatment BioCox (low dose)+BMD+3-Nitro
8. 10x AQ litter treatment–BioCox (half dose)
9. Positive Control BioCox (full dose)+BMD+3-Nitro
10. 4x AQ litter treatment–BioCox (full dose)+BMD+3-Nitro
11. 10x AQ litter treatment–BioCox (half dose)+BMD+3-Nitro
12. 10x AQ litter treatment–BioCox (full dose)+BMD+3-Nitro.

4x Solution of AQ–1 Gallon/44,000sqftx4.2 ml per 48sqft (one pen)
10x Solution of AQ–5 Gallons/44,000sqft=21 ml

TABLE 1

42 Day Data

| Treatment | Weight Gain Kg (42 Days) | Feed Efficiency (42 Days) | Mortality |
|---|---|---|---|
| 1 | 1.877f | 1.945e | 4.025ab |
| 2 | 1.929de | 1.936de | 3.185a |
| 3 | 1.908ef | 1.909cd | 6.992c |
| 4 | 1.922de | 1.937de | 4.683abc |
| 5 | 1.951d | 1.876abc | 6.583bc |
| 6 | 2.050c | 1.904c | 4.464abc |
| 7 | 2.096bc | 1.884bc | 5.531abc |

TABLE 1-continued

42 Day Data

| Treatment | Weight Gain Kg (42 Days) | Feed Efficiency (42 Days) | Mortality |
|---|---|---|---|
| 8 | 1.972d | 1.887bc | 4.252abc |
| 9 | 2.045c | 1.901c | 3.405ab |
| 10 | 2.077c | 1.895bc | 5.311abc |
| 11 | 2.113ab | 1.855a | 4.464abc |
| 12 | 2.153a | 1.857ab | 3.397a |

*values with the same letters are not significantly different

TABLE 2

Intestinal Lesion Scores

| Treatment | 14 Day Scores | 21 Day Scores |
|---|---|---|
| 1 | 2.0c | 1.13d |
| 2 | 2.0c | 0.71abcd |
| 3 | 1.54bc | 1.33d |
| 4 | 0.75a | 0.25abc |
| 5 | 1.33abc | 0.75bcd |
| 6 | 1.71bc | 0.75bcd |
| 7 | 0.96ab | 0.88cd |
| 8 | 1.0ab | 0.42abc |
| 9 | 1.38bc | 0.21abc |
| 10 | 0.67a | 0.38ab |
| 11 | 1.00ab | 0.17abc |
| 12 | 0.88a | 0.65ab |

*values with the same letter are not significantly different

TABLE 3

42 Day Data

| Treatment | Weight | Feed Efficiency | Weight Adjusted Feed Efficiency |
|---|---|---|---|
| 1 | 1.877 | 1.945 | 1.963 |
| 2 | 1.929 | 1.936 | 1.946 |
| 3 | 1.908 | 1.909 | 1.922 |
| 4 | 1.922 | 1.937 | 1.948 |
| 5 | 1.951 | 1.876 | 1.883 |
| 6 | 2.05 | 1.904 | 1.897 |
| 7 | 2.096 | 1.884 | 1.870 |
| 8 | 1.972 | 1.887 | 1.891 |
| 9 | 2.045 | 1.901 | 1.895 |
| 10 | 2.077 | 1.895 | 1.884 |
| 11 | 2.113 | 1.855 | 1.839 |
| 12 | 2.153 | 1.857 | 1.835 |

*standard weight of 2.0 kg
31.78 grams of weight equals 0.01 less KG of feed

Results and Conclusions

Forty-two weight gain for the positive control was significantly improved over the negative control ($p<0.05$). Weight gain for treatment 3 was not different from the negative control. Treatment 5 was significantly improved over the negative control but was significantly less than the positive control ($p<0.05$) at forty two days of age. Treatments 2, 4, and 8 demonstrated significantly improved weight gain over the negative control but were significantly less than the positive control ($p<0.05$). The 42 day weight gains for treatments 6, 7, and 11 were significantly improved ($p<0.05$) over the negative control. Treatments 6 and 7 were not different from the positive control but treatment 11 was significantly improved over the positive control ($p<0.05$). Treatments 10 and 12 were significantly improved over the negative control ($p<0.05$) but only treatment 12 was significantly improved over the positive control for weight gain ($p<0.05$) while treatment 10 was not different from the positive control ($p<0.05$). In this dose titration study it can be concluded that the addition of AQ to the litter tends to improve weight gain numerically. When the 10× AQ dose is used to treat the litter and combined with typically used poultry diets, the weight gain is significantly improved ($p<0.05$) over the positive control.

Feed Conversion for the positive control was significantly improved ($p<0.05$) over the negative control. Treatments 3 and 5 indicated significant ($p<0.05$) improvement if feed efficiency over the negative control but no difference from the positive control. Treatments 2 and 4 were not different from the negative control while treatment 8 was significantly different ($p<0.05$) from the negative control but not different from the positive control for feed efficiency. Treatments 6 and 7 were significantly improved ($p<0.05$) over the negative control and not different form the positive control for feed efficiency. Treatment 11 was significantly improved ($p<0.05$) over both the positive and negative controls for feed efficiency. Treatments 10 and 12 demonstrated a significant ($p<0.05$) improvement in feed efficiency over the negative control. Treatment 10 was not different for the positive control while treatment 12 demonstrated a significant ($p<0.05$) improvement over the positive control. In this dose titration study it can be concluded that when the 10× AQ dose is used to treat the litter and combined with typically used poultry diets, the feed efficiency is significantly improved ($p<0.05$) over the positive control. When the 10× AQ dose is used to treat the litter and the diet contained no coccidiostat or antibiotic feed additive there was a significant difference between this treatment and the negative control ($p<0.05$) and no difference from the positive control.

The 14 day intestinal lesion scores indicated no statistical difference between the positive and negative control ($p<0.05$) indicating that the challenge in the pens was not severe enough to produce lesions in the unmedicated birds. Treatment 4 indicated a significant improvement ($p<0.05$) in lesion score when compared to the positive and negative controls. Treatment 8 while not statistically significant ($p<0.05$) from the positive and negative controls, was biologically significant from the negative control. This means that the lesion score difference was greater than 1 unit (scoring range of 0–4). Treatments 7 and 11 demonstrated significant improvement ($p<0.05$) over the negative control but was the same as the positive control. Treatment 6 was not different for the positive or negative control ($p<0.05$). Treatments 10 and 12 were significantly different from the positive and negative control ($p<0.05$). Based on the 14 day data, it can be concluded that when either the 10× or 4× AQ dose is used to treat the litter and combined with typically used poultry diets, the intestinal coccidia score is improved significantly ($p<0.05$) over the positive and negative control.

When feed efficiency is adjusted for weight, the adjusted feed efficiency demonstrates improvement over the negative control for every treatment (TABLE 3). Statistics can not be run on adjusted feed efficiency.

We claim:

1. A composition comprising litter having a non-toxic anthraquinone compound applied thereon, wherein said anthraquinone is less than approximately 50 micrometers in diameter and wherein the litter is selected from the group consisting of wood shavings, wood chips, wood pellets, sawdust, and sand.

2. A composition comprising litter having a non-toxic anthraquinone compound coated on the surface thereof, wherein said anthraquinone is less than approximately 50 micrometers in diameter and wherein the litter is selected from the group consisting of wood shavings, wood chips, wood pellets, sawdust, and sand.

\* \* \* \* \*